United States Patent
Lenzini et al.

(10) Patent No.: US 11,994,479 B2
(45) Date of Patent: *May 28, 2024

(54) SYSTEM AND METHOD FOR DETERMINING BALE PROPERTIES OF A CROP MATERIAL BALE USING MICROWAVE-BASED SENSING

(71) Applicant: CNH Industrial America LLC, New Holland, PA (US)

(72) Inventors: Nicola Lenzini, Pievepelago (IT); Luca Ferrari, Formigine (IT)

(73) Assignee: CNH Industrial America LLC, New Holland, PA (US)

( * ) Notice: Subject to any disclaimer, the term of this patent is extended or adjusted under 35 U.S.C. 154(b) by 704 days.

This patent is subject to a terminal disclaimer.

(21) Appl. No.: 17/104,879

(22) Filed: Nov. 25, 2020

(65) Prior Publication Data
US 2021/0164921 A1 Jun. 3, 2021

(30) Foreign Application Priority Data
Nov. 28, 2019 (IT) .................. 102019000022422

(51) Int. Cl.
*G01N 22/04* (2006.01)
*G01N 33/02* (2006.01)
(Continued)

(52) U.S. Cl.
CPC ........... *G01N 22/04* (2013.01); *G01N 33/025* (2013.01); *A01F 15/04* (2013.01); *A01F 15/0825* (2013.01)

(58) Field of Classification Search
CPC ....... A01D 43/085; A01F 15/00; A01F 15/04; A01F 15/08; A01F 15/0825; B30B 9/3007; G01N 22/04; G01N 33/025
See application file for complete search history.

(56) References Cited

U.S. PATENT DOCUMENTS 7,330,034 B1 * 2/2008 Pelletier .................. G01N 22/04
324/634
9,861,041 B2 * 1/2018 Verhaeghe ............ A01F 15/042
(Continued)

FOREIGN PATENT DOCUMENTS

AU 2013204543 B1 7/2014
EP 0843959 A1 8/1997
(Continued)

OTHER PUBLICATIONS

Italian Search Report for Italian application 102019000022422 dated Sep. 9, 2020 (5 pages).

*Primary Examiner* — Vinh P Nguyen
(74) *Attorney, Agent, or Firm* — Peter K. Zacharias; Rebecca L. Henkel; Rickard K. DeMille (57) ABSTRACT

A method and system for determining bale properties of crop material bales includes transmitting a first microwave signal through a bale of crop material located within an agricultural baler at a first frequency and transmitting a second microwave signal through the bale of crop material at a different second frequency and calculating, with at least one computing device, a phase angle displacement between the first and second microwave signals and determining, with the at least one computing device, a bale property of the bale of crop material based at least in part on the calculated phase angle differential.

15 Claims, 5 Drawing Sheets

(51) Int. Cl.
   *A01F 15/04*     (2006.01)
   *A01F 15/08*     (2006.01)

(56)     References Cited

U.S. PATENT DOCUMENTS

| | | | |
|---|---|---|---|
| 10,338,088 B2 * | 7/2019 | Verhaeghe | .......... A01F 15/0825 |
| 11,350,572 B2 * | 6/2022 | Rosseel | ............... A01F 15/0825 |
| 11,553,651 B2 * | 1/2023 | Ferrari | .................. A01F 15/101 |
| 2010/0032498 A1 | 2/2010 | Kelly et al. | |

FOREIGN PATENT DOCUMENTS

| | | |
|---|---|---|
| EP | 0950177 B1 | 12/1997 |
| EP | 1053671 A1 | 3/2000 |
| EP | 2446732 A1 | 5/2012 |
| WO | 2016/036749 A1 | 3/2016 |
| WO | 2019/123039 A1 | 6/2019 |

\* cited by examiner

SYSTEM AND METHOD FOR DETERMINING BALE PROPERTIES OF A CROP MATERIAL BALE USING MICROWAVE-BASED SENSING

FIELD OF THE INVENTION

The present subject matter relates generally to agricultural balers, and, more particularly, to systems and methods for estimating or determining one or more bale properties (e.g., moisture content and/or density) of a bale formed with an agricultural baler using microwave sensors.

BACKGROUND OF THE INVENTION

Agricultural balers are used to consolidate and package crop material to facilitate storage and handling of the crop material for later use. In the case of hay, a mower-conditioner is typically used to cut and condition the crop material for windrow drying in the sun. In the case of straw, an agricultural combine discharges non-grain crop material from the rear of the combine (such as wheat or oat straw), which is subsequently picked up by the baler. The cut crop material is typically raked and dried, and a baler, such as a large square baler or round baler, straddles the windrows and travels along the windrows to pick up the crop material and form it into bales. For instance, on a large square baler, a pickup unit at the front of the baler gathers the cut and windrowed crop material from the ground. A packer unit is used to move the crop material from the pickup unit to a duct or pre-compression chamber. For example, the packer unit is typically configured to form a wad or charge of crop material within the pre-compression chamber, which is then transferred to a main baling chamber. Within the main baling chamber, a plunger compresses the charges of crop material to form a bale and, at the same time, gradually advances the bale toward the outlet of the baling chamber.

It is often desirable to obtain information associated with one or more properties of the bales being formed within an agricultural baler, such as the moisture content and/or density, to ensure that a sufficient bale quality is being maintained. For instance, when forming forage bales, it may be necessary to maintain the moisture content within a given range (e.g., 12-20%) to ensure that the bale is sufficiently nutritive, while also avoiding the risk of bale fermentation or self-burning. By determining the moisture content of the bales being formed, appropriate actions may be taken to maintain the desired bale quality, such as by allowing additional time for windrowed crop material within the field to dry in the event it is detected that the bale moisture content is too high.

In this regard, systems have been developed in the past to allow bale properties, such as moisture content, to be estimated or inferred. However, these conventional systems typically rely upon determining the moisture content of a portion of the surface of a bale being formed and then estimating or inferring the overall moisture content of the bale based on the determined surface-level moisture content. Unfortunately, it is often difficult to obtain reliable or accurate measurements using such techniques.

Accordingly, improved systems and related methods for determining one or more bale properties of a crop material bale formed within an agricultural baler would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to a method for determining bale properties of crop material bales. The method includes transmitting a first microwave signal through a bale of crop material located within an agricultural baler at a first frequency and transmitting a second microwave signal through the bale of crop material at a second frequency, with the second frequency of the second microwave signal differing from the first frequency of the first microwave signal. The method also includes calculating, with one or more computing devices, a phase angle displacement between the first and second microwave signals based on detection of the first and second microwave signals as transmitted through the bale of crop material and determining, with the one or more computing devices, one or more bale properties of the bale of crop material based at least in part on the calculated phase angle differential.

In another aspect, the present subject matter is directed to a system for determining bale properties of crop material bales formed within an agricultural baler. The system includes a baling chamber and a sensor assembly configured to transmit first and second microwave signals through a bale of crop material located within the baling chamber at first and second frequencies, respectively, with the first frequency of the first microwave signal differing from the second frequency of the second microwave signal. The system also includes a controller communicatively coupled to the sensor assembly. The controller is configured to receive microwave signal data from the sensor assembly associated with the first and second microwave signals as transmitted through the bale of crop material, calculate a phase angle displacement between the first and second microwave signals based on the microwave signal data, and determine one or more bale properties of the bale of crop material based at least in part on the calculated phase angle differential.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems and methods for determining bale properties of a bale of crop material formed within an agricultural baler. Specifically, in several embodiments, the disclosed system and method utilizes a microwave-based sensor assembly to transmit microwave signals at different frequencies through a bale of crop material disposed within an agricultural baler. The microwave signals transmitted through the bale can then be detected (e.g., by a receiver antenna to the sensor assembly) to allow one or more wave-related properties of the microwave signals to be determined, such as the phase angle of the microwave signals following transmission through the bale. By determining the phase angle of microwave signals transmitted through the bale at two different frequencies, the phase angle differential or displacement between the two frequencies can be calculated, which may then be used to determine the dielectric properties associated with the bale (e.g., the real and imaginary parts of the dielectric constant associated with the bale). Such dielectric properties allow one or more related bale properties to be calculated, such as the moisture content of the bale and/or the density of the bale.

Additionally, in several embodiment, the microwave-based data may be utilized in combination with sensor data from a different sensor technology to improve or assess the accuracy and/or reliability of the estimated bale properties. For instance, in one embodiment, the microwave-based data may be utilized in combination with data received from a near-infrared (NIR) sensor(s). In such an embodiment, the microwave-based data and the NIR-based data may be fused or analyzed together to assess the accuracy and/or reliability of any associated bale properties that have been estimated or inferred in accordance with aspects of the present subject matter.

It should be appreciated that, although the present subject matter is generally described herein with reference to determining bale properties of a bale of crop material formed within an agricultural baler, aspects of the disclosed system and method may also be used to assess or determine the properties of crop material in other contexts or applications. For instance, the microwave-based sensor techniques described herein may also be used to estimate properties of crop material directed through and/or collected within a harvester, such as a combine or forage harvester, such as by using the present subject matter to estimate the moisture content of harvested crops (e.g., grains) stored within the on-board tank of a combine harvester.

Figure 1:
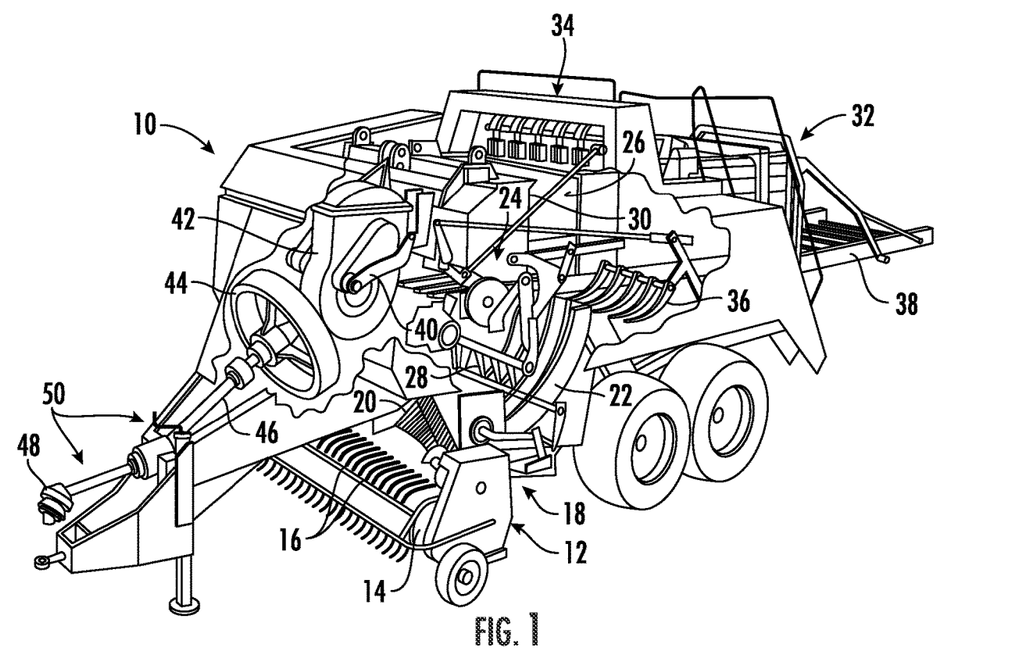
FIG. 1 illustrates a perspective, partially cut-away view of one embodiment of an agricultural baler in accordance with aspects of the present subject matter.
Figure 2:
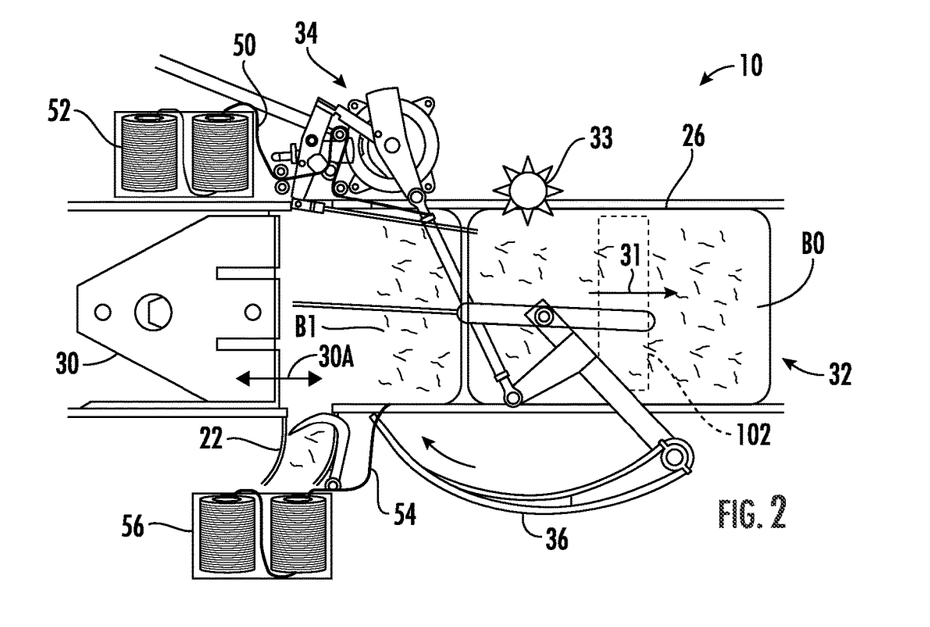
FIG. 2 illustrates a schematic view of an internal baling chamber of the baler shown in FIG. 1, particularly illustrating a microwave sensor assembly provided in operative association with the baling chamber of the baler in accordance with aspects of the present subject matter.

Referring now to the drawings, FIGS. 1 and 2 illustrate differing views of one embodiment of an agricultural baler 10 in accordance with aspects of the present subject matter. Specifically, FIG. 1 illustrates a perspective, partially cut-away view of one embodiment of an agricultural baler 10. Additionally, FIG. 2 illustrates a schematic view of an internal baling chamber of the baler 10 shown in FIG. 1. In the illustrated embodiment, the baler 10 is a configured as a rectangular baler. However, it should be appreciated that, in other embodiments, the baler 10 may have any other suitable baler configuration.

In the illustrated embodiment, the baler 10 is configured to operate using a two-stage feeding system for intaking crop material and forming a bale therefrom. Specifically, crop material is lifted from windrows into the baler 10 using a pickup unit 12. In one embodiment, the pickup unit 12 includes a rotating pickup roll 14 with tines 16 which move the crop rearward toward a packer unit 18. An optional pair of stub augers (one of which is shown, but not numbered) is positioned above the pickup roll 14 to move the crop material laterally inward. Additionally, the packer unit 18 includes packer tines 20 which push the crop into a pre-compression chamber 22 to form a wad or charge of crop material. Specifically, the packer tines 20 intertwine the crop together and pack the crop within the pre-compression chamber 22, with the pre-compression chamber 22 and the packer tines 20 generally functioning as the first stage for crop compression within the baler 10.

Once a sufficient charge of crop material has been formed within the pre-compression chamber 22, a stuffer unit 24 moves the charge of crop material from the pre-compression chamber 22 to a main baling chamber 26 of the baler 10. As shown in FIG. 1, the stuffer unit 24 includes stuffer forks 28 which thrust the charge of crop material directly in front of a plunger 30, which reciprocates back and forth relative to the baling chamber 26 (e.g., as indicated by arrow 30A in FIG. 2) to compress the charge of crop material into a bale. The stuffer forks 28 are returned to their original stationary state after the charge of material has been moved into the baling chamber 26. The plunger 30 compresses the charges of crop to form a bale and, at the same time, gradually advances the bale in a baling direction (e.g., as indicated by arrow 31 in FIG. 2) towards an outlet 32 of the baling chamber 26. The main baling chamber 26 and the plunger 30 generally function as the second stage for crop compression within the baler 10.

It should be appreciated that the plunger 30 may be configured to be actuated relative to the baling chamber 26 using any suitable reciprocation or actuation means known in the art. For instance, in the embodiment shown in FIG. 1, the plunger 30 is connected via a crank arm 40 to a gear box 42. The gear box 42 is driven by a flywheel 44, which, in turn, is connected via a drive shaft 46 with a power take-off (PTO) coupler 48. The PTO coupler 48 is detachably connected with the PTO spline at the rear of the associated traction unit, such as a tractor (not shown). The PTO coupler 48, the drive shaft 46, and the flywheel 44 collectively define a portion of a driveline 50, which provides rotative power to the gearbox 42. The flywheel 44 has a sufficient mass to carry the plunger 30 through a compression stroke as power is applied to the drive shaft 46 by the traction unit (not shown).

As particularly shown in FIG. 2, when a formed bale B0 reaches a predetermined size within the baling chamber 26 (e.g., as determined via a suitable measurement device, such as a star wheel 33), knotters 34 can be actuated which wrap and tie twine (e.g., an upper twine 50 from an upper twine source 52 and a lower twine 54 from a lower twine source 56) around the bale B0 while it is still in the baling chamber 26. Needles 36 are used to bring the lower twine 54 up to the knotters 34 and the tying process takes place. The twine is cut and the formed bale B0 is ejected from a discharge chute 38 (FIG. 1) of the baler as a new bale B1 is being formed within the baling chamber 26.

Additionally, as will be described in greater detail below, in several embodiments, a sensor assembly (indicated by dashed lines 102 in FIG. 2) may be provided in operative association with the baler 10 for sensing or detecting one or more bale properties of the bales being formed therein. Specifically, in accordance with aspects of the present subject matter, the sensor assembly 102 may, in one embodiment, correspond to a microwave-based sensor assembly configured to transmit microwave signals at different frequencies through each bale being formed within the baling chamber 26. The detected parameters of the microwave signals transmitted through each bale may then be used at least in part to estimate or infer one or more bale properties associated with the bale, such as the moisture content and/or the density of the bale.

As shown in FIG. 2, the sensor assembly 102 is generally located within or adjacent to the baling chamber 26, such as by mounting components of the sensor assembly 102 to a wall(s) of the baling chamber 26. As a result, the sensor assembly 102 may be used to detect bale properties of the bale being formed within the chamber 26. However, in other embodiments, the sensor assembly 102 may be positioned at any other suitable location within the baler 10 and/or may be mounted or coupled to any other suitable component of the baler 10 that allows the sensor assembly 102 to generally function as described herein.

Figure 3:
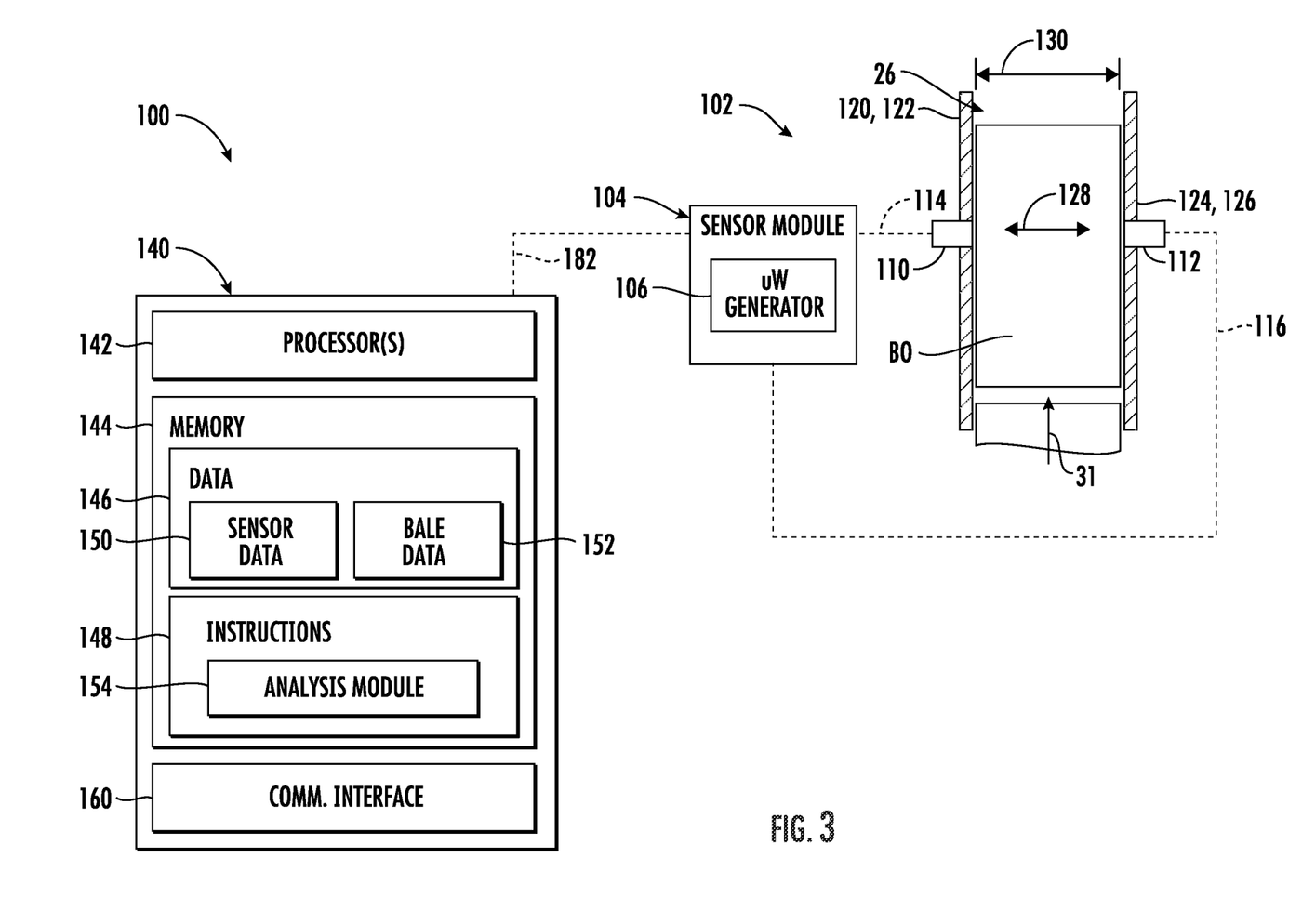
FIG. 3 illustrates a schematic view of one embodiment of a system for determining bale properties of a bale of crop material formed within an agricultural baler in accordance with aspects of the present subject matter.

Referring now to FIG. 3, a schematic view of one embodiment of a system 100 for monitoring or determining one or more bale properties of a bale formed within an agricultural baler is illustrated in accordance with aspects of the present subject matter. For purposes of description, the system 100 will generally be described herein with reference to baler 10 described above with reference to FIGS. 1 and 2. However, it should be appreciated that the disclosed system 100 may generally be utilized with any baler have any suitable baler configuration to monitor one or more bale properties of a bale formed therein.

In general, the system 100 may include a microwave-based sensor assembly 102 configured to both generate microwave signals for transmission through a bale located within an agricultural baler (e.g., baler 10 of FIGS. 1 and 2) and subsequently receive or detect the microwave signals following transmission through the bale. For instance, as shown in FIG. 3, the sensor assembly 102 includes a sensor module 104 having a microwave generator 106 associated therewith for generating variable frequency output signals. Specifically, in accordance with aspects of the present subject matter, the microwave generator 106 may be configured to generate microwave signals at two or more different frequencies (e.g., at 2 GHz and 4 GHz) for transmission through a bale (e.g., bale B0 shown in FIG. 3). Additionally, in one embodiment, the microwave generator 106 may be configured to generate microwave signals across a range of frequencies for transmission through a bale. For instance, the microwave generator 106 may be used to generate microwave signals for performing a frequency sweep during which microwave signals are transmitted through a bale across a range of frequencies (e.g., by increasing from a minimum frequency to a maximum frequency in 50 MHz increments or decrements). It should be appreciated that the sensor module 104 may also include further components for processing and/or analyzing the microwave signals generated by the microwave generator 104 and/or the signals detected by or received back at the sensor module 104. For instance, in one embodiment, the sensor module 104 may include a power divider, a directional coupler, and/or any other suitable components typically included within a radio-frequency (RF) box.

In addition, the sensor assembly 102 includes both a first antenna 110 (hereinafter referred to as the "transmitter antenna") and a second antenna 112 (hereinafter referred as the "receiver antenna") communicatively coupled to the sensor module 104 (e.g., via communicative links 114, 116), with the transmitter antenna 110 being configured to transmit the microwave signals generated by the microwave generator 106 through the adjacent bale B0 and the receiver antenna 112 being configured to receive the microwave signals transmitted through the bale B0 by the transmitter antenna 110. In the illustrated embodiment, the sensor assembly 102 only includes a single pair of antennas 110, 112 for transmitting and receiving microwave signals. However, in other embodiments, the sensor assembly 102 may include any other suitable number of antenna pairs for transmitting and receiving microwave signals, such as two or more antenna pairs. In such embodiments, the transmitter antennas 110 of the various antenna pairs may be configured to be communicatively coupled to a common microwave generator (e.g., the microwave generator 106 shown in FIG. 3) or to respective microwave generators forming part of the sensor module 104 (or of respective sensor modules).

In several embodiments, the transmitter and receiver antennas 110, 112 are configured to be positioned along opposite sides of the bale B0 being formed within the agricultural baler 10, thereby allowing microwave signals to be transmitted from one side of the bale B0 and received on the other side of the bale B0. Specifically, in one embodiment, the transmitter and receiver antennas 110, 112 may be positioned along opposite sides of the baling chamber 26 of the baler 10 such that microwave signals can be transmitted through the bale B0 being formed therein. For instance, as shown in the illustrated embodiment, the transmitter antenna 110 is coupled or positioned relative to or otherwise provided in operative association with a first sidewall 120 defining a first side 122 of the baling chamber 26, while the receiver antenna 112 is coupled or positioned relative to or otherwise provided in operative association with an opposed second sidewall 124 defining an opposite, second side 126 of the baling chamber 26. In such an embodiment, as a bale B0 is being formed within the baling chamber 26, the transmitter antenna 110 may be used to transmit microwave signals from the first side 122 of the baling chamber 26 through the bale B0 for receipt by the receiver antenna 112 at the opposed second side 126 of the baling chamber 26 (e.g., in lateral direction 128 perpendicular to the baling direction 31). As a result, the microwave signals may be transmitted through the entire lateral width of the bale B0

(e.g., width 130 shown in FIG. 3), which may also generally correspond to the lateral width of the baling chamber 26.

It should be appreciated that, in other embodiments, the transmitter and receiver antennas 110, 112 may be disposed at any other suitable location within the baler 10 relative to a bale being formed therein that allows the antennas to generally function as described herein. For instance, as opposed to be located along the lateral sides 112, 126 of the baling chamber 26, the antennas 110, 112 may be positioned along the top and bottom sides of the baling chamber 26 such that microwave signals are transmitted through the bale B0 along its height. Alternatively, the antennas 110, 112 may be positioned along the front and rear ends of the baling chamber 26 such that microwave signals are transmitted through the bale B0 (e.g., in the baling direction 31) along its length.

Moreover, in several embodiments, the system 100 may also include one or more processor-based or computing devices for receiving and subsequently processing the microwave-based data generated by the sensor assembly 102. For instance, as shown in FIG. 3, the system 100 includes a controller 140 communicatively coupled to one or more components of the sensor assembly 102 (e.g., the sensor module 104) for receiving microwave-based data from the sensor assembly 102 associated with the microwave signals transmitted through the bale B0 and detected by the receiver transmitter 112. In such an embodiment, the controller 140 may be configured to analyze the microwave-based data received from the sensor assembly 102 to determine one or more wave-related properties of the microwave signals received by the receiver transmitter 112, such as the wave attenuation and the phase angle of the microwave signals transmitted through a bale and received at the receiver transmitter 112. As will be described below, by determining such wave-related properties for the microwave signals transmitted through a bale of crop material at different frequencies (e.g., two or more different frequencies), the controller 140 may be configured to calculate the dielectric properties of the bale of crop material (e.g., the real and imaginary parts of the dielectric constant associated with the bale) Such dielectric properties may then be used to estimate one or more related bale properties of the bale, such as the moisture content of the bale and/or the density of the bale.

In general, the controller 140 may correspond to any suitable processor-based device(s), such as a computing device or any combination of computing devices. Thus, as shown in FIG. 3, the controller 140 may generally include one or more processor(s) 142 and associated memory devices 144 configured to perform a variety of computer-implemented functions (e.g., performing the methods, steps, algorithms, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory 144 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory 144 may generally be configured to store information accessible to the processor(s) 142, including data 146 that can be retrieved, manipulated, created and/or stored by the processor(s) 142 and instructions 148 that can be executed by the processor(s) 142.

In several embodiments, the data 146 may be stored in one or more databases. For example, the memory 144 may include a sensor database 150 for storing data received from one or more sensors of the disclosed system 100. For example, in one embodiment, the microwave-based data received from the microwave sensor assembly 102 may be stored within the sensor database 150. Additionally, suitable data derived from the microwave-based data may also be stored within the sensor database 150. For instance, in one embodiment, data associated with any wave-related properties of the microwave signals received by the receiver transmitter 112 may be stored within the sensor database 150, such as by storing the wave attenuation and the phase angle of the microwave signals transmitted through each bale at each different frequency within the sensor database 150. It should be appreciated that, in embodiments in which the disclosed system 100 includes additional sensors, the sensor data received from such sensors (or any derived from such sensor data) may similarly be stored within the sensor database 150. For instance, in relation to the embodiment described below with reference to FIG. 4, sensor data received from one or more near-infrared (NIR) sensors 180 and suitable data deriving from such sensor data may be stored within the sensor database 150.

Additionally, as shown in FIG. 3, the memory 144 may include a bale database 152 for storing information related to one or more bale properties determined for each bale being analyzed using the disclosure system 100. For instance, as indicated above, by analyzing the wave-related properties for the microwave signals transmitted through a bale of crop material at different frequencies (e.g., two or more different frequencies), the dielectric properties of the bale (e.g., the real and imaginary parts of the dielectric constant associated with the bale) can be determined, which can then be used to estimate or infer one or more other bale properties for the bale, such as the moisture content of the bale and/or the density of the bale. In such embodiments, the dielectric properties for each bale, along with any bale properties determined using such dielectric properties (e.g., bale moisture and density), may be stored within the bale database 152. It should be appreciated that, in embodiments in which the disclosed system 100 is configured to estimate or infer one or more bale properties based on non-microwave-based data, such additional bale property data may similarly be stored within the bale database 152. For instance, in relation to the embodiment described below with reference to FIG. 4, bale property data (e.g., moisture content data) estimated or inferred based on the sensor data received from one or more near-infrared (NIR) sensors 180 may also be stored within the bale database 152.

Referring still to FIG. 3, in several embodiments, the instructions 148 stored within the memory 144 of the controller 140 may be executed by the processor(s) 142 to implement a data analysis module 154. In general, the data analysis module 154 may be configured to analyze the data received from any sensors of the disclosed system 100. Specifically, in several embodiments, the data analysis module 154 may be configured to analyze the microwave-based data received from the microwave sensor assembly 102 to determine one or more wave-related properties of the microwave signals transmitted through the bale and subsequently received by the receiver antenna 112. For instance, in one embodiment, the data analysis module 154 may be configured to compare the amplitude of the microwave signal received at the receiver antenna 112 to the original amplitude of the microwave signal transmitted from the transmitter antenna 110 to determine the reduction in amplitude of the signal as it was transmitted through the bale B0 (i.e., the wave attenuation). In addition to the wave attenuation, the data analysis module 154 may be configured to analyze the microwave-based data to determine the phase angle of the microwave signal received at the receiver antenna 112 (e.g., using known signal analysis techniques). As indicated above, in several embodiments, the system 100 may be used to transmit microwave signals through each bale being analyzed at two or more different frequencies. Thus, it should be appreciated that the data analysis module 154 may, for example, be configured to calculate the wave attenuation and phase angle associated with the microwave signals transmitted through the bale at each frequency.

Moreover, in several embodiments, the data analysis module 154 may also be configured to determine one or more bale properties of the bale being analyzed based on the wave-related properties of the microwave signals transmitted through the bale, such as the wave attenuation and phase angle at each frequency. Specifically, as will be described in greater detail below, the data analysis module 154 may be configured to calculate the dielectric properties associated with the bale being analyzed based on both the phase angle displacement of the microwave signals transmitted through the bale at the differing frequencies and the wave attenuation of the microwave signals. Such dielectric properties may then be used to estimate or infer one or more additional bale properties associated with the bale, such as the moisture content or the density of the bale.

It should be appreciated that, although the data analysis module 154 is generally described herein as forming an integral portion of or otherwise being executed by the controller 140, the data analysis module 154 may, instead, form part of and/or may be configured to be executed by a separate processor-based device, such as a separate computing device. In such an embodiment, the data analysis module 154 (as included within or executed by the separate processor-based device) may be communicatively coupled to the controller 140 such that data may be transmitted between such devices, such as data received and/or generated by the data analysis module 154.

Additionally, it should be appreciated that, in several embodiments, the controller 140 may be configured to actively control the operation of the microwave generator 106 of the sensor assembly 102. For instance, the controller 140 may be configured to control the operation of the microwave generator 106 such that microwave signals of differing frequencies are transmitted through each bale B0 being analyzed. Specifically, in one embodiment, the controller 140 may be configured to control the operation of the microwave generator 106 such that a first microwave signal is initially transmitted through the bale B0 at a first frequency (e.g., 2 GHz) and then a second microwave signal is transmitted through the bale B0 at a second frequency (e.g., 4 GHz) that differs from the first frequency. By transmitting microwave signals through the bale B0 at the differing frequencies, microwave-based data may be collected at each frequency, thereby allowing the desired bale properties to be determined in accordance with aspects of the present subject matter.

It should also be appreciated that, in one embodiment, the controller 140 may be configured to control the operation of the microwave generator 106 such that microwave signals are generated as part of a frequency sweep across which signals are transmitted through a bale B0 at various incremental or decremental frequencies. For instance, the controller 140 may control the operation of the microwave generator 106 such that a first or initial microwave signal is transmitted through the bale B0 at a first or initial frequency (e.g., 2 GHz). Thereafter, the operation of the microwave generator 106 may be controlled such that the frequency of the microwave signals transmitted through the bale B0 is increased (or decreased) in predetermined incremental amounts (or decremental amounts) from the first or initial frequency to a second or final frequency. By incrementally or decrementally adjusting the frequency of the microwave signals across a range of frequencies, a larger dataset can be collected for the various different frequencies, which can then be used to more accurately determine the desired bale properties in accordance with aspects of the present subject matter.

Moreover, as shown in FIG. 3, the controller 140 may also include a communications interface 160 to provide a means for the controller 140 to communicate with any of the various other system components described herein. For instance, one or more respective communicative links or interfaces 162 (e.g., one or more data buses) may be provided between the communications interface 160 and the sensor assembly 102 to allow microwave-based data to be transmitted from the sensor assembly 102 to the controller 140 and/or to allow the controller 140 to transmit control signals to the sensor assembly 102 for controlling the operation of the microwave generator 106.

As indicated above, by determining the wave-related properties of the microwave signal transmitted through a bale, the dielectric properties of the bale may be determined. Specifically, the real part of the dielectric constant may be determined as a function of the differential or displacement of the phase angles of the microwave signals at the differing frequencies. For instance, both the phase angle differential between two microwave signals transmitted at differing frequencies through a bale of crop material and the real part of the dielectric constant of such bale can be expressed as a function of the velocity of the wave through the bale. Such expressions are provided below as Equations 1 and 2:

$$\Delta\varphi(f_1, f_2) = 2\pi(\Delta f)\frac{d}{v} \quad (1)$$

$$v = \frac{c}{\sqrt{\varepsilon'}} \quad (2)$$

wherein, $\Delta\varphi$ corresponds to the phase angle displacement or differential between the phase angles ($\varphi$) detected for a microwave signal transmitted through a bale at a first frequency ($f_1$) and a microwave signal transmitted through the bale at a second frequency ($f_2$), $\Delta f$ corresponds to the differential or difference between the first frequency ($f_1$) and the second frequency ($f_2$), d corresponds to the distance between the microwave transmitter and the microwave receiver (e.g., the bale width 130), v corresponds to the velocity of the microwave signals through the bale, c corresponds to the speed of light, and $\varepsilon'$ corresponds to the real part of the dielectric constant associated with the bale.

By substituting the right side of Equation 2 (i.e., the speed of light (c) divided by the square root of the real part of the dielectric constant ($\varepsilon'$)) into Equation 1 for the wave velocity (v), the phase angle differential ($\Delta\varphi$) and the real part of the dielectric constant ($\varepsilon'$) can be expressed as a function of each other within a single mathematical relationship. For example, by solving the resulting equation for the real part of the dielectric constant (ε'), such dielectric property can be expressed as a function of the phase angle differential (Δφ) and the frequency differential (Δf) (Equation 3):

$$\varepsilon' = \left[\frac{\Delta\varphi c}{2\pi \Delta f d}\right]^2 \quad (3)$$

Thus, by detecting the phase angle of a microwave signal transmitted through a bale at two known frequencies, the real part of the dielectric constant associated with the bale can be calculated. The real part of the dielectric constant can then be used to calculate the imaginary part of the dielectric constant associated with the bale based on the determined wave attenuation for one of the microwave signals. For instance, the imaginary part of the dielectric constant for the bale can be calculated using the following expression (Equation 4):

$$\varepsilon'' = \frac{-A\lambda_0}{8.686\pi d}\sqrt{\varepsilon'} \quad (4)$$

wherein, ε" corresponds to the imaginary part of the dielectric constant associated with the bale, A corresponds to the determined wave attenuation for microwave signals transmitted at the first frequency ($f_1$) or the second frequency ($f_2$), $\lambda_0$ corresponds to the wavelength of the microwave signal transmitted though the bale, d corresponds to the distance between the microwave transmitter and the microwave receiver (e.g., the bale width 130), and ε' corresponds to the real part of the dielectric constant associated with the bale.

Based on the determined dielectric properties associated with the bale, values for both the moisture content of the bale and the density of the bale may be calculated. Specifically, as is generally understood by those of ordinary skill in the art, a direct correlation (e.g., a quadratic relationship) may be established between the dielectric properties associated with the bale and the moisture content within the bale. Similarly, as is generally understood by those of ordinary skill in the art, a direct correlation (e.g., a linear relationship) may be established between the dielectric properties associated with the bale and the density of the bale. Thus, by determining the associated dielectric properties, the system controller 140 (e.g., the data analysis module 154) may calculate both a moisture content value and a density value for each bale being analyzed within the baler 10. Such moisture/density values may then be stored within the controller's memory 144 as described above (e.g., with the bale database 152).

It should be appreciated that the correlation or relationship between the dielectric properties and the bale moisture content and between the dielectric properties and the bale density may be stored within the controller 140 in any suitable form or fashion that allows the controller 140 to calculate the corresponding moisture content and density values for the bale being analyzed. For instance, such correlations or relationships may be stored as mathematical formulas or expressions or may be stored as suitable look-up tables within the controller's memory 144. Additionally, it should be appreciated that the relevant correlations or relationships may be established via routine experimentation. For instance, experimental trials may be conducted with various bales of known moisture content and density to establish the desired correlations or relationships between the dielectric properties and the bale moisture/density.

Figure 4:
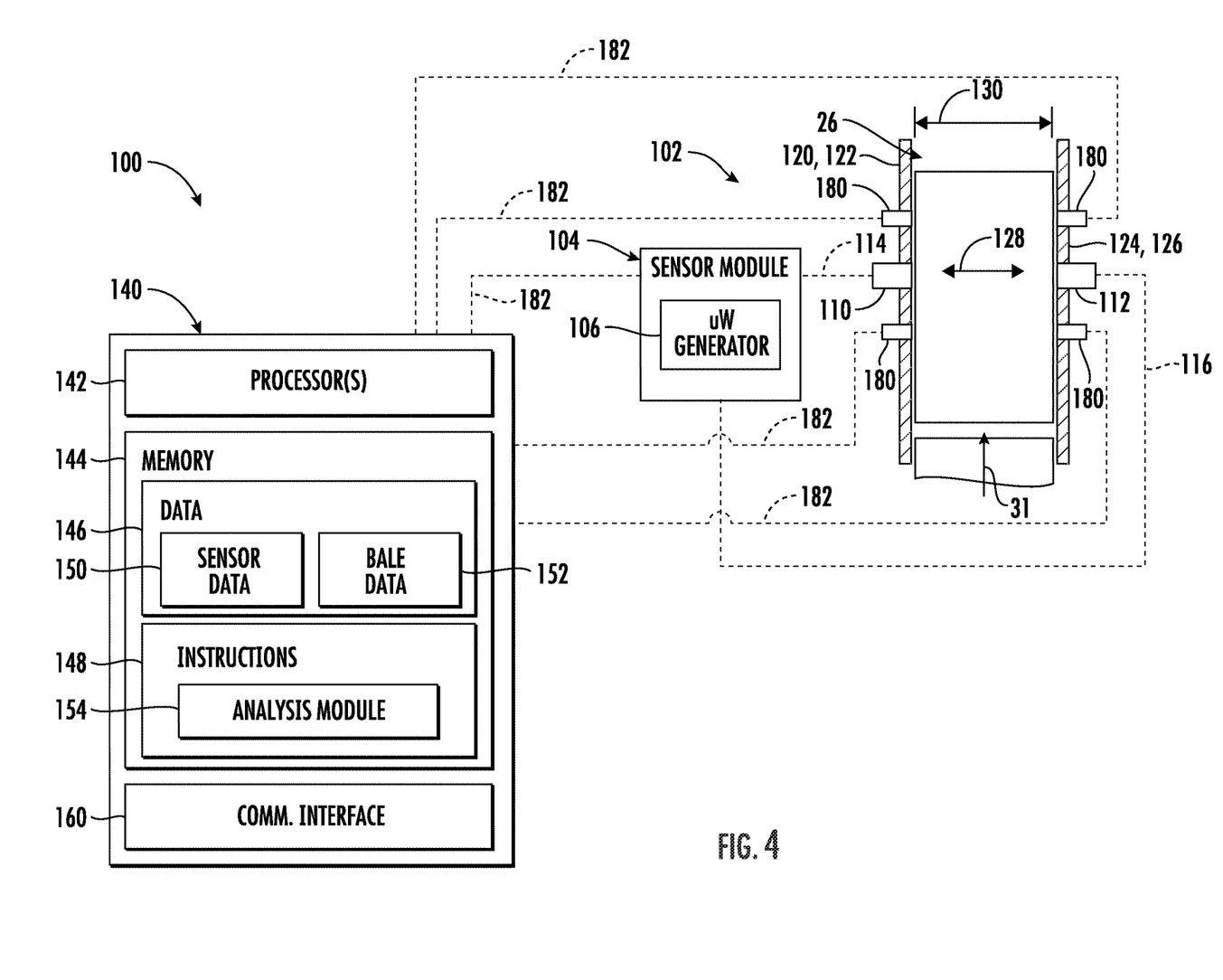
FIG. 4 illustrates a schematic view of another embodiment of a system for determining bale properties of a bale of crop material formed within an agricultural baler in accordance with aspects of the present subject matter.

Referring now to FIG. 4, a schematic view of another embodiment of the system 100 described above with reference to FIG. 3 is illustrated in accordance with aspects of the present subject matter. In general, the system 100 shown in FIG. 4 may include the same or similar system components to those described above with reference to FIG. 3. For instance, in the embodiment shown in FIG. 4, the system 100 includes both the microwave sensor assembly 102 and the controller 140 described above with reference to FIG. 3. In such an embodiment, it should be appreciated that such system components may generally function the same as or similar to that described above with reference to FIG. 3.

Additionally, as shown in FIG. 4, the system 100 includes one or more near-infrared (NIR) sensors 180 configured to generate NIR-based data associated with one or more bale properties of the bale B0 being analyzed. Specifically, in several embodiments, the NIR sensor(s) 180 may be configured to transmit energy waves (e.g., light waves) within the NIR region of the electromagnetic spectrum (e.g., 780 nm to 2500 nm) towards the adjacent surface of the bale B0 and detect the reflection of such energy waves from the bale surface. The reflected waves received back at the NIR sensor(s) 180 may then be analyzed to determine one or more local bale properties associated with the area at or adjacent to the surface at which the waves were reflected. For instance, the data deriving from the NIR sensor(s) 180 may be used to determine a local moisture content and/or a local density of the bale B0 of the area at or adjacent to the associated reflection surface.

It should be appreciated that the system 100 may include any suitable number of NIR sensors 180 configured to provide localized data associated with the bale B0 being analyzed. For instance, in the illustrated embodiment, the system 100 includes four NIR sensors 180 spaced apart around the baling chamber 26, with two NIR sensors 180 being positioned along each side 122, 126 of the baling chamber 26. Specifically, as shown in FIG. 4, two NIR sensors 180 are coupled or positioned relative to or otherwise provided in operative association with the first sidewall 120 of the baling chamber 26, while two additional NIR sensors 180 are coupled or positioned relative to or otherwise provided in operative association with the opposed second sidewall 124 of the baling chamber 26. As a result, localized NIR-based data may be generated at differing locations along each side of the bale B0. However, in other embodiments, the system 100 may include less than four NIR sensors (including a single NIR sensors) or greater than four NIR sensors. Additionally, it should be appreciated that the NIR sensor(s) 180 may be positioned at any other suitable location within the baler 10 and/or may be mounted or coupled to any other suitable component of the baler 10 that allows the sensor(s) 180 to function as described herein.

As shown in FIG. 4, each NIR sensor 180 is communicatively coupled to the controller 140 (e.g., via links 182) such that the NIR-based data generated by each sensor 180 may be transmitted to the controller 140 for subsequent processing and/or analysis. For instance, the NIR-based data received from the NIR sensors 180 may be stored within the controller's memory 144 (e.g., the sensor database 150) along with the microwave-based data received from the microwave sensor assembly 102. Additionally, similar to that described above in relation to the microwave-based data, the controller 140 may be configured to analyze the NIR-based data to determine or estimate one or more localized bale properties for the bale B0 being analyzed. For instance, the data analysis module 154 may be configured to analyze the NIR-based data to determine local moisture content values and/or local density values for the bale. Such bale properties values may then be stored within the controller's memory 144 (e.g., within the bale database 152). Additionally, in embodiments including two or more NIR sensors 180, the local bale property values determined as a function of the NIR-based data may be averaged to calculate an average local moisture content value and/or an average local density value for the bale B0.

By including the NIR sensor(s) 180, the controller 140 may be configured to determine both microwave-based bale properties and NIR-based bale properties for each bale B0 being analyzed within the baler 10. Specifically, in several embodiments, the controller 140 may be configured to utilize the sensor data received from the microwave sensor assembly 102 to determine a microwave-based moisture content value and/or a microwave-based density value for the bale B0 being analyzed, while the controller 140 may also be configured to utilize the sensor data received from the NIR sensor(s) 180 to determine a NIR-based moisture content value and a NIR-based density value for the bale B0 being analyzed. In such embodiments, the bale properties determined using the different sensor technologies may be analyzed to further increase the accuracy of the system 100 or otherwise provide more reliable bale property data.

Figure 5:
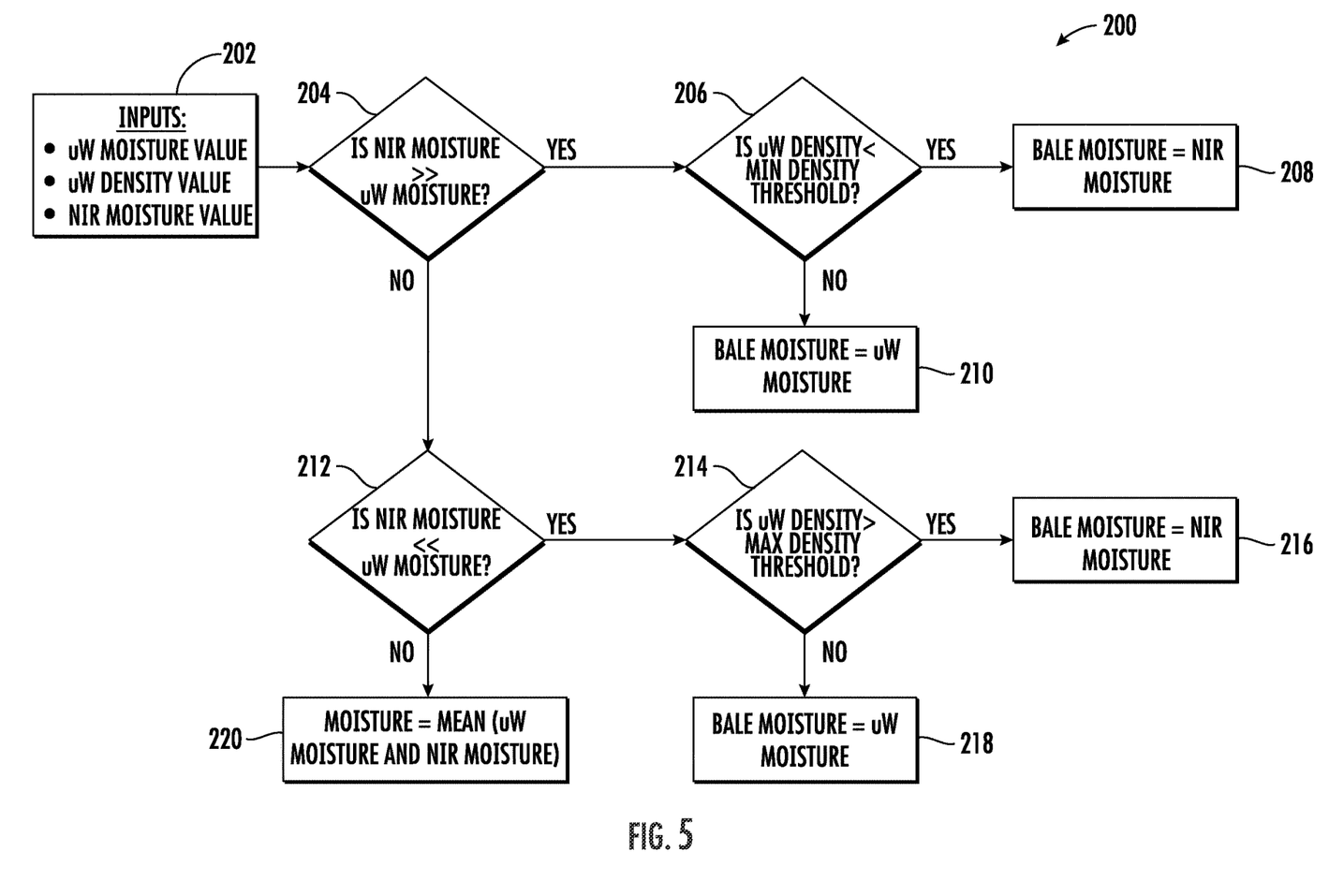
FIG. 5 illustrates a flow diagram of one embodiment of a control algorithm for analyzing sensor data received from different sensor types to determine which dataset likely provides the most reliable or accurate bale property data in accordance with aspects of the present subject matter.

For instance, FIG. 5 illustrates an exemplary flow diagram of one embodiment of a control algorithm 200 for analyzing the bale properties determined as a function of both the microwave-based data and the NIR-based data to determine which dataset likely provides the most reliable or accurate moisture data. It should be appreciated that the algorithm 200 may, for example, be automatically executed by the controller 140, such as by the data analysis module 154, as part of the data processing functionality of the disclosed system 100.

As shown in FIG. 5, at 202, the algorithm 200 utilizes several inputs associated with bale properties determined using the microwave-based data received from the microwave sensor assembly 102 or the NIR-based data received from the NIR sensor(s) 180. Specifically, the algorithm 200 utilizes two bale properties determined using the microwave-based data, namely a microwave-based moisture content value (i.e. "uW moisture") and a microwave-based density value (i.e., uW density) for a given bale being analyzed, and one bale property determined using the NIR-based data, namely an NIR-based moisture content value (i.e. "NIR moisture") for such bale.

As shown in FIG. 5, at 204, the NIR-based moisture content value is compared to the microwave-based moisture content value to determine if the NIR-based moisture content value is substantially greater than the microwave-based moisture content value. Such an assessment may be made by determining if the NIR-based moisture content value is greater than the microwave-based moisture content value by a predetermined threshold (e.g., a predetermined differential or a predetermined percentage).

In the event the NIR-based moisture content value is greater than the microwave-based moisture content value by the predetermined threshold (and thus, the NIR-based moisture content value is substantially greater than the microwave-based moisture content value), at 206, it is determined whether the microwave-based density value is less than a predetermined minimum density threshold. For example, a predetermined density range may be defined that covers the range of expected or anticipated density values for a bale formed within the agricultural baler 10, with the range extending from a minimum density threshold to a maximum density threshold. In this regard, at 206, the microwave-based density value is compared to the minimum density threshold associated with the predetermined density range. As shown in FIG. 5, if the microwave-based density value is less than the minimum density threshold, it may be assumed that the difference in moisture values determined at 204 is due to the microwave data being inaccurate or unreliable. As a result, at 208, the NIR-based moisture content value is selected as the final or most reliable moisture content value for the bale being analyzed. Alternatively, if the microwave-based density value is not less than the minimum density threshold, it may be assumed that the difference in moisture values determined at 204 is due to the NIR data being inaccurate or unreliable. As a result, at 210, the microwave-based moisture content value is selected as the final or most reliable moisture content value for the bale being analyzed.

As shown in FIG. 4, in the event it is determined at 204 that the NIR-based moisture content value is not greater than the microwave-based moisture content value by the predetermined threshold (and thus, the NIR-based moisture content value is not substantially greater than the microwave-based moisture content value), then, at 212, the NIR-based moisture content value is compared to the microwave-based moisture content value to determine if the NIR-based moisture content value is substantially less than the microwave-based moisture content value. Such an assessment may be made by determining if the NIR-based moisture content value is less than the microwave-based moisture content value by a predetermined threshold (e.g., a predetermined differential or a predetermined percentage).

In the event the NIR-based moisture content value is less than the microwave-based moisture content value by the predetermined threshold (and thus, the NIR-based moisture content value is substantially less than the microwave-based moisture content value), at 214, it is determined whether the microwave-based density value is greater than a predetermined maximum density threshold. As indicated above, a predetermined density range may be defined that covers the range of expected or anticipated density values for a bale formed within the agricultural baler 10, with the range extending from a minimum density threshold to a maximum density threshold. In this regard, at 214, the microwave-based density value is compared to the maximum density threshold associated with the predetermined density range. As shown in FIG. 5, if the microwave-based density value is greater than the maximum density threshold, it may be assumed that the difference in moisture values determined at 212 is due to the microwave data being inaccurate or unreliable. As a result, at 216, the NIR-based moisture content value is selected as the final or most reliable moisture content value for the bale being analyzed. Alternatively, if the microwave-based density value is not greater than the maximum density threshold, it may be assumed that the difference in moisture values determined at 212 is due to the NIR-based data being inaccurate or unreliable. As a result, at 218, the microwave-based moisture content value is selected as the final or most reliable moisture content value for the bale being analyzed.

Moreover, as shown in FIG. 5, in the event it is determined at 212 that the NIR-based moisture content value is not less than the microwave-based moisture content value by the predetermined threshold (and thus, the NIR-based moisture content value is neither substantially greater than nor substantially less than the microwave-based moisture content value per the assessments made at 204 and 212), it may be assumed that both the microwave-based data and the NIR-based data is accurate or reliable. In such instance, both values may be used to determine a final moisture content value for the bale being analyzed. For instance, in one embodiment, the final moisture content value for the bale may be set as the mean or average of the NIR-based and microwave-based moisture content values.

Figure 6:
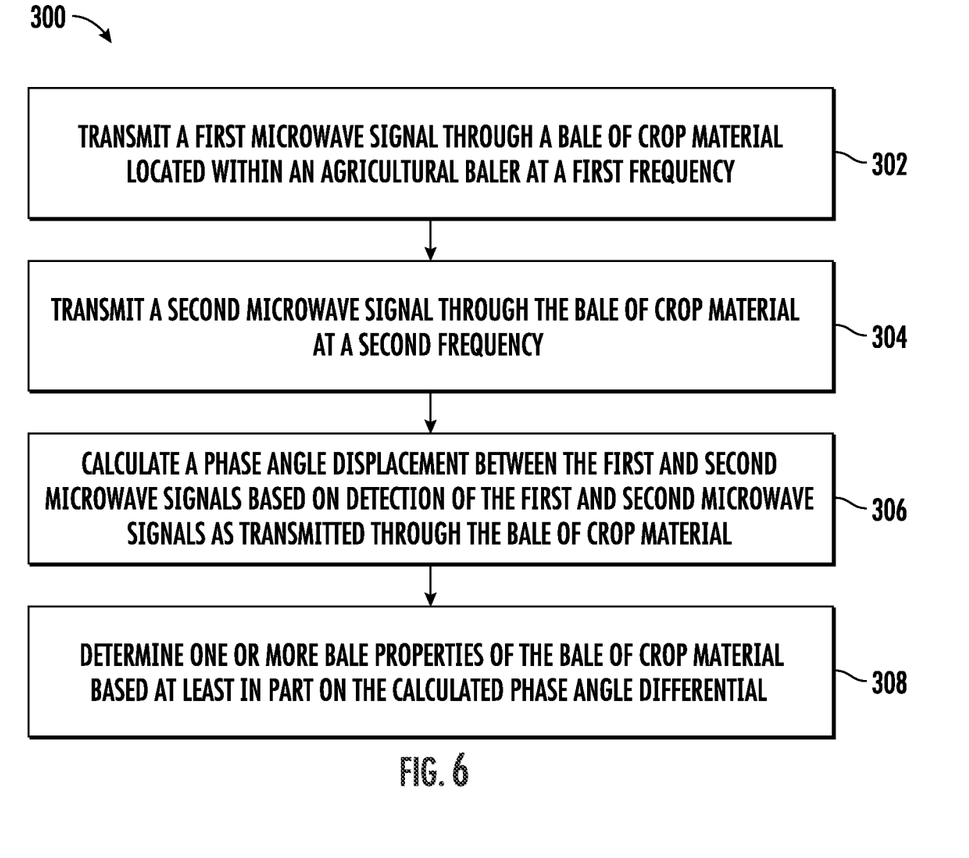
FIG. 6 illustrates a flow diagram of one embodiment of a method for monitoring bale properties of a bale of crop material formed within an agricultural baler in accordance with aspects of the present subject matter.

Referring now to FIG. 6, a flow diagram of one embodiment of a method 300 for determining bale properties of crop material bales formed within an agricultural baler is illustrated in accordance with aspects of the present subject matter. In general, the method 300 will be described herein with reference to the baler 10 and the embodiments of the system 100 described above with reference to FIGS. 1-5. However, it should be appreciated by those of ordinary skill in the art that the disclosed method 300 may generally be implemented with any agricultural baler having any suitable baler configuration and/or any system having any suitable system configuration. In addition, although FIG. 6 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIGS. 6, at (302) and (304), the method 300 includes transmitting first and second microwave signals through a bale of crop material located within an agricultural baler at first and second frequencies, respectively. Specifically, as indicated above, a microwave sensor assembly 102 may be used to generate microwave signals at different frequencies (e.g., across a range of frequencies) for transmission through a bale to be analyzed, such as the current bale B0 being formed within the baling chamber 26 of the baler 10. Additionally, as indicated above, the microwave signals transmitted through the bale B0 may be received by a component of the sensor assembly 102 (e.g., the receiver transmitter 112) and corresponding microwave-based data may be transmitted from the sensor assembly 102 to the controller 140 for subsequent processing and/or analysis.

Additionally, at (306), the method 300 includes calculating a phase angle displacement between the first and second microwave signals based on detection of the first and second microwave signals as transmitted through the bale of crop material. Specifically, as indicated above, the controller 140 may be configured to analyze the microwave-based data received from the sensor assembly 104 to determine one or more wave-related properties associated with the microwave signals detected by the receiver antenna 112, such as the phase angle and wave attenuation of each signal transmitted through the bale and subsequently received by the receiver antenna of the sensor assembly. The controller 140 may then be configured to determine the phase angle displacement by calculating a differential between the phase angles for the microwave signals transmitted through the bale at the different frequencies.

Moreover, at (308), the method 300 includes determining one or more bale properties of the bale of crop material based at least in part on the calculated phase angle differential. For example, as indicated above, the phase angle differential may be used to determine the real part of the dielectric constant associated with the bale, which, in turn, can be used in combination with the determined wave attenuation to calculate the imaginary part of the dielectric constant associated with the bale. Such dielectric properties may then be used by the controller 140 to determine one or more related bale properties of the bale being analyzed, such as the moisture content of the bale and/or the density of the bale.

It is to be understood that the steps of the method 300 are performed by the controller 140 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 140 described herein, such as the method 300, is implemented in software code or instructions which are tangibly stored on a tangible computer readable medium. The controller 140 loads the software code or instructions via a direct interface with the computer readable medium or via a wired and/or wireless network. Upon loading and executing such software code or instructions by the controller 140, the controller 140 may perform any of the functionality of the controller 140 described herein, including any steps of the method 300 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

The invention claimed is:

1. A method for determining bale properties of a baled crop material, the method comprising:
    transmitting a first microwave signal through a bale of crop material located within an agricultural baler at a first frequency;
    transmitting a second microwave signal through the bale of crop material at a second frequency, wherein the second frequency is different from the first frequency;
    calculating, with one or more computing devices, a phase angle displacement between the first and second microwave signals based on detection of the first and second microwave signals as transmitted through the bale of crop material, and
    determining, with the one or more computing devices, one or more bale properties of the bale of crop material based at least in part on the calculated phase angle differential.

2. The method of claim 1, further comprising forming the bale of crop material within a baling chamber of the agricultural baler;
wherein transmitting the first and second microwave signals through the bale of crop material comprises transmitting the first and second microwave signals through the bale of crop material while the bale of crop material is located within the baling chamber of the agricultural baler.

3. The method of claim 1, further comprising determining a wave attenuation of at least one of the first microwave signal or the second microwave signals as transmitted through the bale of crop material;
wherein determining the one or more bale properties of the bale of crop material comprises determining the one or more bale properties of the bale of crop material based at least in part on the calculated phase angle differential and the wave attenuation of the at least one of the first microwave signal or the second microwave signal.

4. The method of claim 3, further comprising determining at least one dielectric property of the bale of crop material based on the phase angle differential between the first and second phase angles and the wave attenuation of the at least one of the first microwave signal or the second microwave signal;
wherein determining the one or more bale properties of the bale of crop material comprises determining the one or more bale properties of the bale of crop material based on the at least one dielectric property of the bale of crop material.

5. The method of claim 1, wherein determining the one or more bale properties of the bale of crop material comprises determining at least one of a moisture content of the bale of crop material or a density of the bale of crop material based at least in part on the calculated phase angle differential.

6. The method of claim 1, further comprising:
receiving, with the one or more computing devices, data from a near-infrared (NIR) sensor indicative of the one or more properties of the bale of crop material located within the agricultural baler; and
determining, with the one or more computing devices, an NIR-based moisture content value for the bale of crop material based at least in part on the data received from the NIR sensor;
wherein the determining the one or more properties of the bale of the crop material comprises determining a microwave-based moisture content value for the bale of crop material based at least in part on the calculated phase angle differential.

7. The method of claim 6, further comprising:
determining whether the NIR-based moisture content value differs from the microwave-based moisture content value for the bale of crop material by at least a predetermined differential threshold;
when the NIR-based moisture content value differs from the microwave-based moisture content value for the bale of crop material by at least the predetermined differential, comparing a sensor-based bale density value for the bale of crop material to at least one bale density threshold associated with a predetermined density range; and
selecting one of the microwave-based moisture content value or the NIR-based moisture content value as a final moisture content value for the bale of crop material based on the comparison of the sensor-based bale density value to the at least one bale density threshold.

8. The method of claim 6, further comprising:
determining whether the NIR-based moisture content value differs from the microwave-based moisture content value for the bale of crop material by at least a predetermined differential threshold; and
determining a final moisture content value for the bale of crop material based on both the microwave-based moisture content value and the NIR-based moisture content value when the NIR-based moisture content value does not differ from the microwave-based moisture content value for the bale of crop material by at least the predetermined differential threshold.

9. The method of claim 1, wherein transmitting the first and second microwave signals through the bale of crop material comprises transmitting microwave signals through the bale of crop material at different incremental or decremental frequencies.

10. A system for determining bale properties of crop material bales formed within an agricultural baler including a baling chamber, the system comprising:
a sensor assembly configured to transmit first and second microwave signals through a bale of crop material located within the baling chamber at first and second frequencies, respectively, the first frequency of the first microwave signal differing from the second frequency of the second microwave signal;
a controller communicatively coupled to the sensor assembly, the controller being configured to:
receive microwave signal data from the sensor assembly associated with the first and second microwave signals as transmitted through the bale of crop material;
calculate a phase angle displacement between the first and second microwave signals based on the microwave signal data; and
determine one or more bale properties of the bale of crop material based at least in part on the calculated phase angle differential.

11. The system of claim 10, wherein the sensor assembly comprises a transmitter antenna configured to transmit the first and second microwave signals through the bale of crop material and a receiver transmitter configured to receive the first and second microwave signals as transmitted through the bale of crop material.

12. The system of claim 10, wherein the controller is further configured to determine a wave attenuation of at least one of the first microwave signal or the second microwave signal as transmitted through the bale of crop material.

13. The system of claim 12, wherein the controller is further configured to determine at least one dielectric property of the bale of crop material based on the phase angle differential between the first and second phase angles and the wave attenuation of the at least one of the first microwave signal or the second microwave signal, the controller further configured to determine the one or more bale properties of the bale of crop material based on the at least one dielectric property of the bale of crop material.

14. The system of claim 10, wherein the controller is configured to transmit microwave signals through the bale of crop material at different incremental or decremental frequencies as part of a frequency sweep.

15. The system as in any of claim 10, further comprising a near-infrared (NIR) sensor communicatively coupled to the controller and configured to provide data indicative of the one or more properties of the bale of crop material.

* * * * *